(12) United States Patent
Wada et al.

(10) Patent No.: US 9,204,790 B2
(45) Date of Patent: Dec. 8, 2015

(54) IMAGE PROCESSING APPARATUS FOR FUNDUS IMAGE, IMAGE PROCESSING METHOD FOR FUNDUS IMAGE, AND PROGRAM MEDIUM

(75) Inventors: Manabu Wada, Kawasaki (JP); Akihiro Kushida, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 192 days.

(21) Appl. No.: 13/557,089

(22) Filed: Jul. 24, 2012

(65) Prior Publication Data
US 2013/0028484 A1    Jan. 31, 2013

(30) Foreign Application Priority Data

Jul. 29, 2011 (JP) .................................. 2011-167057
Jun. 27, 2012 (JP) .................................. 2012-144324

(51) Int. Cl.
*A61B 3/12* (2006.01)
*A61B 3/00* (2006.01)

(52) U.S. Cl.
CPC ................. *A61B 3/12* (2013.01); *A61B 3/0025* (2013.01)

(58) Field of Classification Search
CPC ......... A61B 3/00; G06K 9/4652; H04N 1/60; H04N 1/6027; H04N 1/4074; H04N 1/4078; G06T 2207/10024; G06T 2207/30216; G09G 2300/0452; G09G 2320/066
USPC ................................................. 382/106, 128
See application file for complete search history.

(56) References Cited

U.S. PATENT DOCUMENTS

2005/0238230 A1* 10/2005 Yoshida ........................ 382/167
2006/0280361 A1* 12/2006 Umeda ......................... 382/167
2010/0303345 A1* 12/2010 Reid et al. .................... 382/163
2011/0058063 A1*  3/2011 Lee ............................. 348/223.1

FOREIGN PATENT DOCUMENTS

| CN | 001765119 A | 4/2006 |
| CN | 001881234 A | 12/2006 |
| JP | H03-063031 A | 3/1991 |
| JP | 2002-238859 A | 8/2002 |
| JP | 2003-310554 A | 11/2003 |
| JP | 2009-165624 A | 7/2009 |

\* cited by examiner

*Primary Examiner* — Amir Alavi
*Assistant Examiner* — Kenny Cese
(74) *Attorney, Agent, or Firm* — Canon USA Inc. IP Division (57) ABSTRACT

A image processing apparatus includes a selection unit configured to select either first color tone conversion processing or second color tone conversion processing having a ratio of red wavelength component set lower than either blue wavelength or green wavelength components with respect to the first color tone conversion processing, and a color tone conversion unit configured to convert a color of a fundus image by the selected color tone conversion processing.

15 Claims, 11 Drawing Sheets

| COLOR TONE CONVERSION PROCESSING | IMAGE ADJUSTMENT VALUE | | | | | |
|---|---|---|---|---|---|---|
| | LUMINANCE | CONTRAST | GAMMA | COLOR TONE (RED) | COLOR TONE (GREEN) | COLOR TONE (BLUE) |
| FIRST COLOR TONE CONVERSION PROCESSING | 0 | 0 | 10 | 5 | 0 | 0 |
| SECOND COLOR TONE CONVERSION PROCESSING | 10 | 0 | 10 | 0 | 0 | 0 |

FIG. 11

IMAGE PROCESSING APPARATUS FOR FUNDUS IMAGE, IMAGE PROCESSING METHOD FOR FUNDUS IMAGE, AND PROGRAM MEDIUM

BACKGROUND OF THE INVENTION

1. Field of the Invention

The present invention relates to image processing of an ophthalmic apparatus, and more particularly to color tone conversion processing of a fundus image.

2. Description of the Related Art

Conventionally, to acquire a color fundus image for diagnosis, there has been known an image processing apparatus that performs image processing such as color tone conversion processing or gamma processing for an original image captured by an image sensor. The color tone conversion processing means conversion of a color tone of each of red, green and blue channels of the original image by a predetermined correction value. Japanese Patent Application Laid-Open No. 2003-310554 discusses a technique in which an ophthalmic imaging apparatus automatically sets, when a photographic light source is selected, a predetermined correction value corresponding to the selected photographic light source at each channel of the original image, and provides an image where a color temperature of the photographic light source has been corrected.

Concerning an auto-white balance technology discusses in a general digital camera or digital video camera, there is a technology for causing the correction value set to each channel of the original image to automatically follow, and performing color tone conversion processing so that a color tone of an object is set to a predetermined color tone.

Melanin pigment is present between a pigment epithelial layer and a choroid of the fundus. It is known that the amount of melanin pigment varies according to individual difference. In an object where the amount of melanin pigment is large, when it is irradiated with illumination light from the photographic light source, apart of the illumination light is absorbed following absorption of the melanin pigment, thus causing less reflection from the choroid. On the other hand, in an object where the amount of melanin pigment is small, reflection from the choroid is greater. The reflection from the choroid is subjected to imaging by the red channel of the image. Accordingly, in the object where the amount of melanin pigment is small, the image is redder than that in the object where the amount of melanin pigment is large.

Japanese Patent Application Laid-Open No. 2009-165624 discusses a technique in which an image where a gradation value at each of the red, green and blue channels of the captured image can be equal to or higher than a predetermined gradation value by adjusting an optical filter inserted into an illumination system of a photographic light source or a photographic light amount of the photographic light source. The optical filter is provided to correct the influence on the image according to a melanin pigment amount.

However, in the case of the method discussed in Japanese Patent Application Laid-Open No. 2003-310554, the white balance is automatically adjusted according to the photographic light source, and thus all subject's eyes become a predetermined color tone. As a result, while adjusting the white balance enables correction of the influence on the image according to the melanin pigment amount, the image captured is one where a color tone difference according to individual difference, which is important diagnostic information for diagnosing the fundus image, has been lost.

The technology discussed in Japanese Patent Application Laid-Open No. 2009-165624 compensates for the individual difference by the color tone of the light source. A wavelength distribution of the illumination light applied to each object accordingly varies from one object to another. Thus, a diagnostic purpose to acquire information on the individual difference under the same photographic environment is not always appropriate. Further, a plurality of optical filters and a dynamic range of a photographic light amount are necessary, and thus the apparatus is enlarged.

SUMMARY OF THE INVENTION

The present invention is directed to a mechanism for acquiring an image suited for diagnosis by reducing the influence on the image according to a melanin pigment amount.

According to an aspect of the present invention, a image processing apparatus includes the following components: a selection unit configured to select a first color tone conversion processing and a second color tone conversion processing for correcting the influence, according to melanin pigment amount, on an image with respect to an fundus image captured by an image sensor, and a color tone conversion unit configured to convert a color tone of a fundus image by color tone conversion processing selected by the selection unit.

Further features and aspects of the present invention will become apparent from the following detailed description of exemplary embodiments with reference to the attached drawings.

BRIEF DESCRIPTION OF THE DRAWINGS

The accompanying drawings, which are incorporated in and constitute a part of the specification, illustrate exemplary embodiments, features, and aspects of the invention and, together with the description, serve to explain the principles of the invention.

DESCRIPTION OF THE EMBODIMENTS

Various exemplary embodiments, features, and aspects of the invention will be described in detail below with reference to the drawings.

Figure 1:
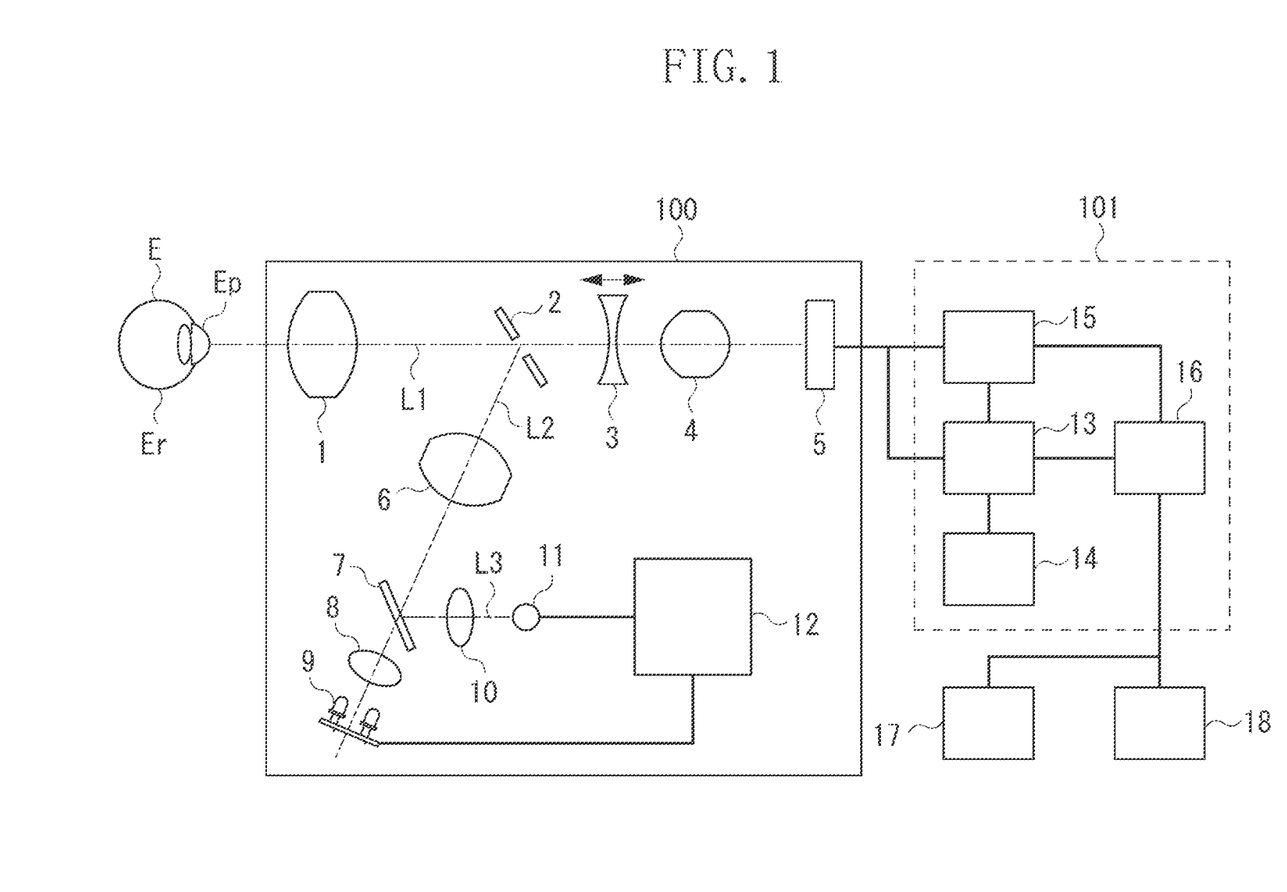
FIG. 1 illustrates a configuration of an ophthalmic image capture system according to a first exemplary embodiment.

A first exemplary embodiment will be described. Hereinafter, the first exemplary embodiment of the present invention will be described with reference to the accompanying drawings. FIG. 1 illustrates a configuration example of an ophthalmic image capture system according to the first exemplary embodiment. The ophthalmic image capture system includes a fundus camera 100 and an image processing apparatus 101 according to the present invention.

First, a configuration of the fundus camera 100 will be described. On an optical axis L1 opposite a fundus Er of a subject's eye E, there are sequentially arranged an objective lens 1, then a perforated mirror 2, a focus lens 3, an imaging lens 4, and an image sensor 5. These components constitute a photographing optical system for the subject's eye E.

On the other hand, on an optical axis L2 in a reflection direction of the perforated mirror 2, there are arranged a lens 6, a dichroic mirror 7, a condenser lens 8, and an observation light source 9. In addition, on an optical axis L3 in a reflection direction of the dichroic mirror 7, there are arranged a condenser lens 10 and a photographing light source 11. The components on the optical axes L2 and L3 constitute an illumination optical system. The dichroic mirror 7 has characteristics of transmitting a wavelength range of the observation light source 9 while reflecting a wavelength range of the photographing light source 11. The observation light source 9, in which a plurality of light-emitting diodes (LED) is disposed, is a light source which irradiates the subject's eye with fixed light. The photographing light source 11 is a light source which irradiates the fundus Er with visible photographing pulse light.

The fundus camera 100 additionally includes a fundus camera control unit 12. The fundus camera control unit 12 is connected to the observation light source 9 and the photographing light source 11 to control light emission amount and light emission time of the observation light source 9 and the photographing light source 11.

Next, a configuration of the image processing apparatus 101 will be described. Each block of the image processing apparatus 101 illustrated in FIG. 1 is a functional block realized by executing a program by a central processing unit (CPU) 110 (not illustrated). It is a program module loaded to a random access memory (RAM) to be executed by an operation system (OS) or a host module that uses the program module when image processing is carried out.

The image processing apparatus 101 includes a color tone conversion unit 13 that converts a color tone of the fundus image, and a color tone selection unit 14 that selects a color tone to be converted by the color tone conversion unit 13. The image processing apparatus 101 further includes a monochrome conversion unit 15 that converts the fundus image into a single color, and a gradation conversion unit 16 that converts a gradation of the fundus image.

The color tone conversion unit 13 converts image data acquired by the image sensor 5 in the fundus camera 100 by the color tone selected by the color tone selection unit 14. Gradation conversion is performed on the color-tone-converted image by the gradation conversion unit 16. The monochrome conversion unit 15 converts the image data acquired by the image sensor 5 in the fundus camera 100 into a monochrome, and the gradation conversion unit 16 converts gradation of the converted image. These components may be configured with circuit configuration. The image gradation-converted by the gradation conversion unit 16 is then displayed on a display unit 17 and stored in a storage unit 18.

Hereinafter, a flow of fundus photographing in the above described configuration of the ophthalmic image capture system will be described. A photographer positions the subject's eye E in front of the objective lens 1, and executes precise alignment or focusing with the subject's eye E for fundus photographing. When the fundus camera control unit 12 lights the observation light source 9, the observation light passes through the illumination optical system from the observation light source 9 to the objective lens 1, and illuminates the fundus Er via a pupil Ep of the subject's eye E.

Reflected light from the fundus Er illuminated by the observation light source 9 passes through the photographing optical system from the objective lens 1 through the perforated mirror 2 and the focus lens 3 to the imaging lens 4 to reach the image sensor 5. An observation original image captured by the image sensor 5 is subjected to monochromization processing by the monochrome conversion unit 15, and then subjected to calculation for gamma curve or contrast by the gradation conversion unit 16 to be displayed on the display unit 17.

The photographer executes precise alignment between the subject's eye E and the fundus camera 100 by operating an operation stick (not illustrated) while watching an observation image displayed on the display unit 17 to vertically and horizontally move the fundus camera 100, and executes focusing by operating a focus knob (not illustrated) to move the focus lens 3.

Next, a photographing is operated as follows. After checking as to accurate alignment and focusing, the photographer operates a photographing start switch (not illustrated) to photograph the fundus Er. The operation of the photographing start switch causes the photographing light source 11 to emit light. The photographing light emitted from the photographing light source 11 passes through the illumination optical system from the photographing light source 11 to the objective lens 1, and illuminates the fundus Er. Reflected light from the fundus Er illuminated by the photographing light source 11 passes through the photographing optical system from the objective lens 1 through the perforated mirror 2 and the focus lens 3 to the imaging lens 4 to reach the image sensor 5. A photographing original image captured by the image sensor 5 is subjected to color tone conversion processing by the color tone conversion unit 13, and then subjected to calculation for gamma curve or contrast by the gradation conversion unit 16 to be displayed on the display unit 17 under control of a display control unit (not illustrated), and recorded in the recording unit 18.

Figure 2:
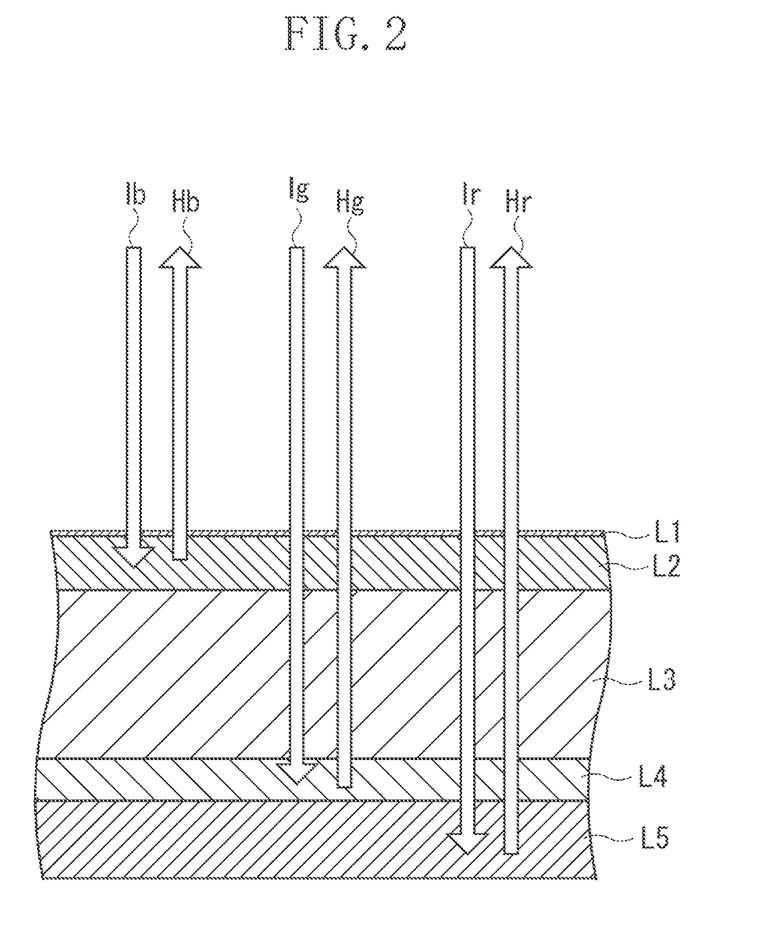
FIG. 2 illustrates reflection of illumination light by a photographic light source on a fundus Er.

Referring to FIG. 2, the reflection of the illumination light by the photographing light source 11 on the fundus Er will be described. FIG. 2 illustrates, in a simplified manner, a structure of the fundus in a depth direction, which includes, from a vitreous body side illustrated in an upper side, an inner boundary membrane L1, a nerve fiber layer L2, a plurality of layers L3 from an inner plexiform layer to a stratum neuroepithleliale retinae, a pigment epithelial layer L4, and a choroid L5. The illumination light of the photographing light source 11 includes a red wavelength Ir, a green wavelength Ig, and a blue wavelength Ib. In addition, the reflected light of the illumination light includes a red wavelength Hr, a green wavelength Hg, and a blue wavelength Hb.

The illumination light of the photographing light source 11 varies in invasion depth to the fundus Er according to wavelength. Specifically, the red wavelength Ir of the illumination light reaches the choroid L5 to be reflected as the red wavelength Hr of the reflected light on the choroid L5. The green wavelength Ig of the illumination light reaches the pigment epithelial layer L4 of the retina to be reflected as the green wavelength Hg of the reflected light on the pigment epithelial layer L4. The blue wavelength Ib of the illumination light reaches the nerve fiber layer L2 of the retina to be reflected as the blue wavelength Hb of the reflected light on the nerve fiber layer L2. The red wavelength, the blue wavelength, and the green wavelength are wavelength bands corresponding to the red channel, the blue channel and the green channel of the image sensor.

Accordingly, captured images capturing the reflected light Hr, Hg, and Hb are different in information to be represented among the channels. Specifically, much information from the choroid L5 is represented in the red channel of the captured image capturing the red wavelength Hr of the reflected light. Much information from the pigment epithelial layer L4 is represented in the green channel of the captured image capturing the green wavelength Hg of the reflected light. Much information from the nerve fiber layer L2 is represented in the blue channel of the captured image capturing the blue wavelength Hb of the reflected light.

Further, melanin pigment is present between the pigment epithelial layer L4 and the choroid L5. The amount of melanin pigment is known to vary according to individual difference. In a subject's eye where the amount of melanin pigment is small, when it is irradiated with illumination light from the photographic light source 11, absorption of the red wavelength Hr of the illumination light absorbed by the melanin pigment is small, and the red wavelength Hr of the reflected light from the choroid is consequently greater. On the other hand, in a subject's eye where the amount of melanin pigment is normal, absorption of the red wavelength Hr of the illumination light absorbed by the melanin pigment is greater than that of the subject's eye where the amount of melanin pigment is small, and the red wavelength Hr of the reflected light from the choroid is consequently smaller. Thus, in the subject's eye where the amount of melanin pigment is small, compared with the subject's eye where the amount of melanin pigment is normal, the red channel is greater than the green and blue channels of the image, and the image is redder.

According to the present invention, focusing on the amount of melanin pigment, all the subject's eyes are roughly classified into two groups, namely, a group where the amount of melanin pigment is normal, and a group where the amount of melanin pigment is small. The former is referred to as a first group, and the latter is referred to as a second group.

Next, the color tone conversion unit 13 and the color tone selection unit 14 will be described. For color tone conversion processing carried out by the color tone conversion unit 13 according to the present invention, there are first color tone conversion processing for the first group of subject's eyes, and second color tone conversion processing for the second group of subject's eyes.

The color tone selection unit 14 is used by the photographer to select processing of one of the first color tone conversion processing and the second color tone conversion processing. The color tone selection unit 14 enables the photographer to select which processing to perform by, for example, a user interface. According to a selection result of the color tone selection unit 14, the color tone conversion unit 13 executes processing of one of the first color tone conversion processing and the second color tone conversion processing.

Hereinafter, each of the first color tone conversion processing and the second color tone conversion processing will be described. In the first color tone conversion processing, a fixed correction value is set for each of the red, green and blue channels of the original image captured by the image sensor 5, and a color tone is converted by executing calculation based on the correction value.

The following images are acquired by the calculation based on the fixed correction value for the first color tone conversion processing. When first color tone conversion processing is carried out for a representative subject's eye belonging to the first group, processed image is referred to as an image P1. The image P1 includes a red channel R1, a green channel G1, and a blue channel B1. When first color tone conversion processing is carried out for a representative subject's eye belonging to the second group, processed image is referred to as an image P2. The image P2 includes a red channel R2, a green channel G2, and a blue channel B2.

Then, a ratio of the red channel to the green channel of the image P1 (R1/G1) is represented by TH1<R1/G1<TH2. In the ranges TH1 and TH2, information of the choroid represented in the red channel is represented with a good balance with respect to information of the pigment epithelial layer represented in the green channel. Further, a ratio of the red channel to the blue channel of the image P1 (R1/B1) is represented by TH3<R1/B1<TH4. In the ranges TH3 and TH4, information of the choroid represented in the red channel is represented with a good balance with respect to information of the nerve fiber layer represented in the blue channel.

A ratio R2/G2 of the red channel with respect to the green channel of the image P2 is represented by R2/G2>TH2, and a ratio R2/B2 of the red channel with respect to the blue channel is represented by R2/B2>TH4.

Thus, the fixed correction value for the first color tone conversion processing enables, in the subject's eye belonging to the first group where the amount of melanin pigment is normal, acquisition of an image where information of the choroid is within TH1, TH2, TH3, TH4 with respect to information up to the nerve fiber layer and the pigment epithelial layer, and in the subject's eye belonging to the second group where the amount of melanin pigment is small, an image where information of the choroid is greater than TH2 and TH4 with respect to the information up to the nerve fiber layer and the pigment epithelial layer.

Since the first color tone conversion processing includes the calculation based on the fixed correction value, a color tone difference between the subject's eyes according to individual difference can be represented. In the second color tone conversion processing, a fixed correction value is set for each of the red, green and blue channels of the original image captured by the image sensor 5, and a color tone is converted by executing calculation based on the correction value.

The following images are acquired for the first group by the calculation based on the fixed correction value for the second color tone conversion processing. When second color tone conversion processing is carried out for a representative subject's eye belonging to the first group, the processed image is referred to as an image P3. The image P3 includes a red channel R3, a green channel G3, and a blue channel B3. When second color tone conversion processing is carried out for a representative subject's eye belonging to the second group, the processed image is referred to as an image P4. This image P4 has a red channel R4, a green channel G4, and a blue channel B4.

Then, a ratio of the red channel to the green channel of the image P3 (R3/G3) is represented by R3/G3<TH1. Further, a ratio of the red channel to the blue channel of the image P3 (R3/B3) is represented by R3/B3<TH3. A ratio of the red channel to the green channel of the image P4 (R4/G4) is represented by TH1<R4/G4<TH2, and a ratio of the red channel with respect to the blue channel (R4/B4) is presented by TH3<R4/B4<TH4.

Thus, the fixed correction value for the second color tone conversion processing enables, in the subject's eye belonging to the second group where the amount of melanin pigment is great, acquisition of an image where information of the choroid is within TH1, TH2, TH3, TH4 with respect to information up to the nerve fiber layer and the pigment epithelial layer, and in the subject's eye belonging to the first group where the amount of melanin pigment is normal, an image where information of the choroid is smaller than TH1 and TH3 with respect to the information up to the nerve fiber layer and the pigment epithelial layer.

Since the second color tone conversion processing includes the calculation based on the fixed correction value, an color tone difference between the subject's eyes according to individual difference can be represented.

Specifically, the fixed correction value for the second color tone conversion processing is only required to be set so that when the same subject's eye is photographed, a ratio of a red channel to green and blue channels of an image captured in the second color tone conversion processing is lower than that of the image captured in the first color tone conversion processing, and the ration is within TH1, TH2, TH3, and TH4.

Any one of the following three methods for setting the fixed correction value for the second color tone conversion processing may be employed. The methods will be described by using the image P2 where the representative subject's eye of the second group is subjected to the first color tone conversion processing and the image P4 where the subject's eye is subjected to the second color tone conversion processing.

According to the first setting method, a fixed correction value is set so that a red channel, a green channel, and a blue channel of the image P4 become R4<R2, G4=G2, and B4=B2 with respect to the image P2, and its ratio becomes within TH1, TH2, TH3, and TH4.

According to the second setting method, a fixed correction value is set so that the red channel, the green channel, and the blue channel of the image P4 become R4<R2, G4>G2, and B4>B2 with respect to the image P2, and its ratio becomes within TH1, TH2, TH3, and TH4.

According to the third setting method, a fixed correction value is set so that the red channel, the green channel, and the blue channel of the image P4 become R4=R2, G4>G2, and B4>B2 with respect to the image P2, and the ratio becomes within TH1, TH2, TH3, and TH4.

The image thus subjected to the color tone conversion processing is then subjected to calculation for gamma curve or contrast by the gradation conversion unit 16 to be displayed on the display unit 17 and recorded in the recording unit 18.

Simultaneously when the processed image is displayed on the display unit 17, information to enable identification as to which of the first color tone conversion processing and the second color tone conversion processing has been executed is displayed. This provides high usability to the photographer because the photographer can immediately know which of the processes the image has been subjected to. Images separately subjected to the first color tone conversion processing and the second color tone conversion processing can both be displayed on the display unit 17. Such display selection is executed by a display selection unit 130 (not illustrated).

The fixed value set for the second color tone conversion processing by any one of the three setting methods should advisably be set to a value so that when the same subject's eye is photographed, a luminance value Y of the image after the first color tone conversion processing and a luminance value Y of the image after the second color tone conversion processing can be prevented from being changed. It is because luminance information of the image is important diagnostic information in fundus diagnosis. This arrangement is particularly suited when the images separately subjected to the first color tone conversion processing and the second color tone conversion processing are both displayed on the display unit 17.

The luminance value Y of the image, which indicates a luminance component, is generally represented by $Y=0.2990 \times R+0.5870 \times G+0.1140 \times B$. Accordingly, in the first method, all R, G and B values of the image after the second color tone conversion processing are set larger than those of the image after the first color tone conversion processing.

In the second method, all the R, G and B values of the image after the second color tone conversion processing are appropriately adjusted. Thus, in the third method, all the R, G and B values of the image after the second color tone conversion processing are reduced with respect to the image after the first color tone conversion processing.

Simultaneously when the processed image is stored in the storage unit 18, information to enable identification as to which of the first color tone conversion processing and the second color tone conversion processing has been executed is stored. This provides high usability to the photographer because, when watching the image again after a while from the capturing, the photographer can immediately know which of the processes the image has been subjected to.

As described above, by switching the first color tone conversion processing and the second color tone conversion processing to correct the influence on the image according to the amount of melanin pigment, a fundus image where a balance of information is high up to the nerve fiber layer, the pigment epithelial layer, and the choroid in all the subject's eyes can be provided. Since each of the first color tone conversion processing and the second color tone conversion processing includes the calculation based on the fixed value, a fundus image where a color tone difference between the subject's eyes is represented can be provided. Further, the above image can be provided by the simple configuration of the image processing apparatus.

In the exemplary embodiment, the color tone selection unit 14 is used by the photographer to select the processing. However, a color tone can be selected by referring to subject's information input during the photographing.

In the exemplary embodiment, the subject's eyes are divided into the two groups according to the amounts of melanin pigment, and the first color tone conversion processing and the second conversion processing corresponding to the groups are provided. However, the amounts of melanin pigment of the subject's eyes may be further subdivided, and a plurality of color tone conversion processes corresponding to the subdivided groups may be provided.

In the exemplary embodiment, the image processing apparatus 101 is disposed separately from the fundus camera 100. However, the image processing apparatus 101 may be included in the fundus camera control unit 12 in the fundus camera 100. Further, the present invention can be realized by executing the following processing. Specifically, software (program) for realizing the embodiment is supplied to a system or an apparatus via a network or various storage media, and a computer (or CPU micro processing unit (MPU)) of the system or the apparatus reads the program to execute it.

Figure 3:
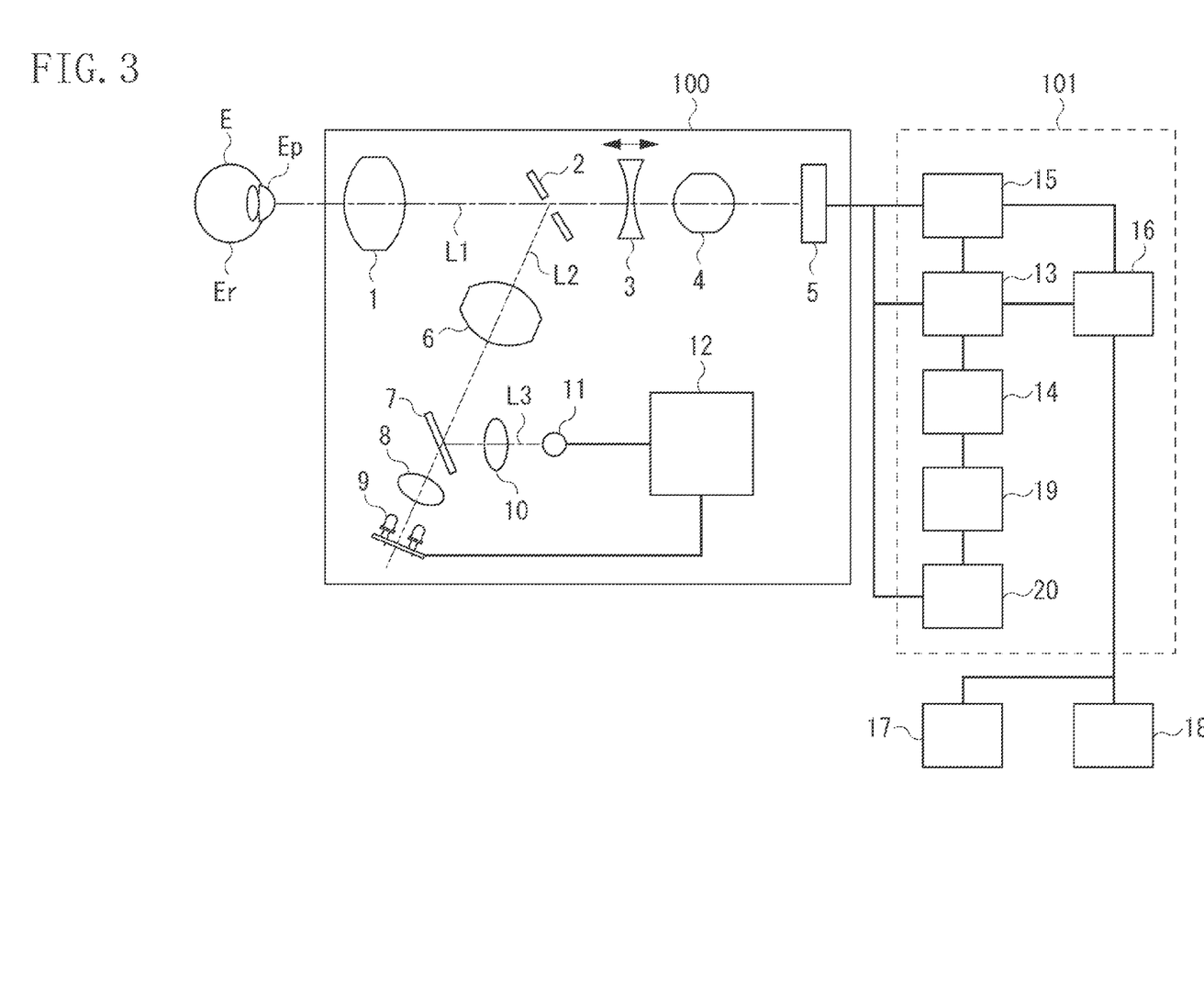
FIG. 3 illustrates a configuration of an ophthalmic image capture system according to a second exemplary embodiment.

A second exemplary embodiment will be described. FIG. 3 illustrates a configuration of the second exemplary embodiment. Components similar to those illustrated in FIG. 1 are denoted by similar reference numerals, and description thereof is omitted. In FIG. 3, in addition to the components illustrated in FIG. 1, there are arranged a range acquisition unit 20 and a detection unit 19. The range acquisition unit 20 is connected to an image sensor 5 and the detection unit 19. The detection unit 19 is connected to a color tone selection unit 14.

Figure 5:
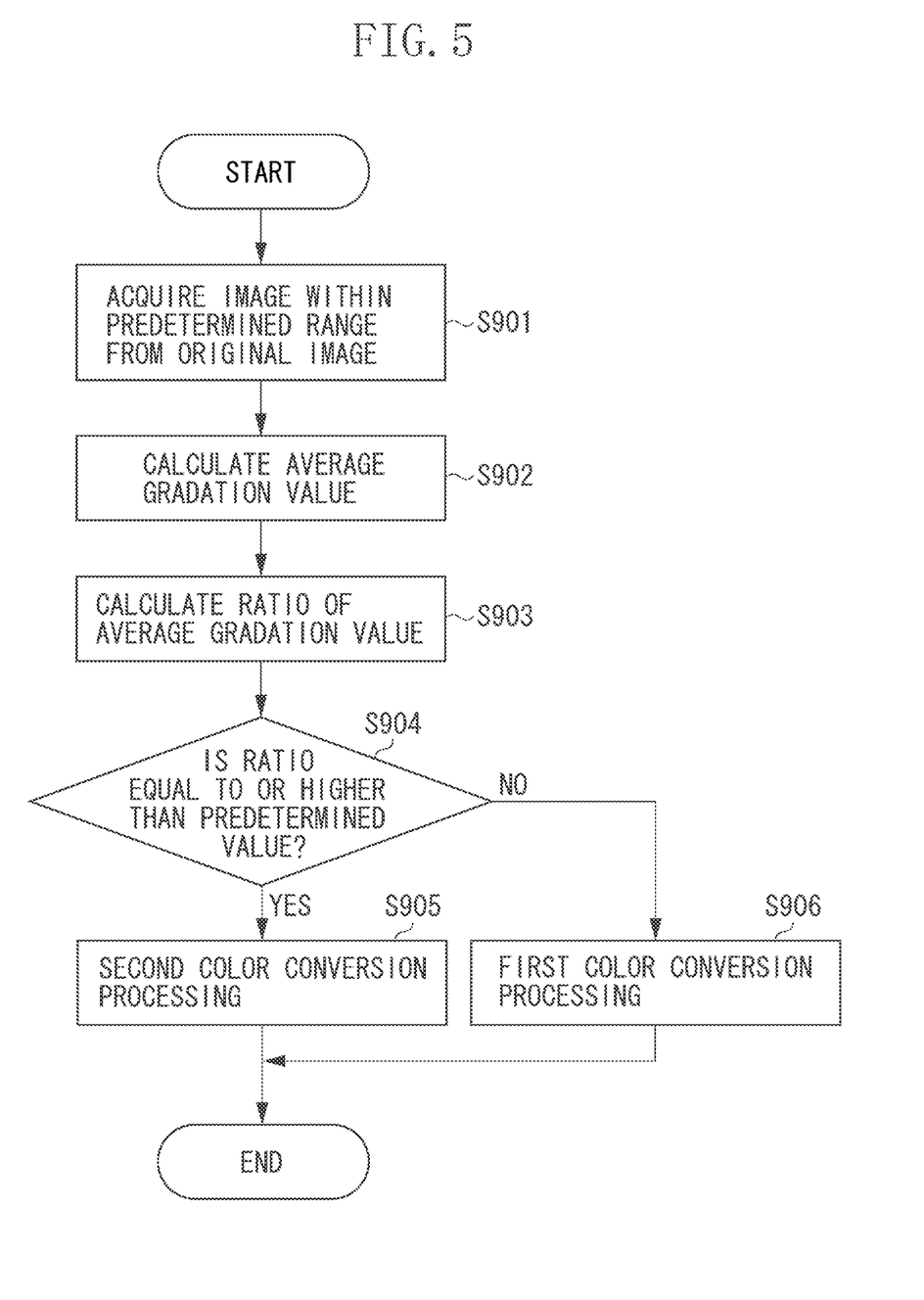
FIG. 5 is a flowchart illustrating an operation of an image processing apparatus according to the second exemplary embodiment.

Referring to a flowchart of FIG. 5, operations of the range acquisition unit 20, the detection unit 19, the color tone section unit 14, and a color tone conversion unit 13 will be described. When an original image is captured by the image sensor 5, the range acquisition unit 20 acquires an image within a predetermined range from the original image.

Figure 4:
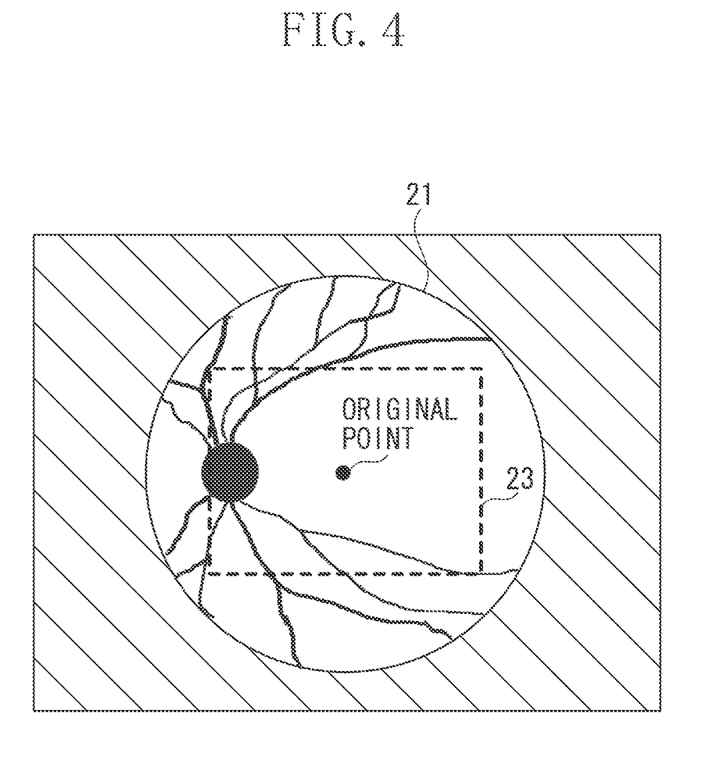
FIG. 4 illustrates a range of an image acquired by a range acquisition unit.

FIG. 4 illustrates a range of an image acquired by the range acquisition unit 20 with respect to the original image. An image of a predetermined range 23 around the center of the original image is acquired. The image acquired by the range acquisition unit 20 is reoffered to as P5 and has a number of pixels (M, N).

In step S901, the range acquisition unit 20 acquires a range where only a fundus is represented not including a mask 21 in a fundus image.

At least a portion where a nerve fiber layer, a pigment epithelial layer, and a choroid are represented is acquired. On the other hand, a range where only a blood vessel or a papillary portion is represented is not acquired. It is because the blood vessel or the papillary portion lacks melanin pigment.

In step S902, the detection unit 19 first calculates an average gradation value for each of red, green and blue channels of the image P5 acquired by the range acquisition unit 20. Average gradation values $R5_{ave}$, $G5_{ave}$, and $B5_{ave}$ of the red, green and blue channels R5, G5, and B5 of the image P5 are represented as follows.

$$R5_{ave} = \frac{1}{M \times N} \sum_{j=1}^{N} \sum_{i=1}^{M} R5(i, j)$$

$$G5_{ave} = \frac{1}{M \times N} \sum_{j=1}^{N} \sum_{i=1}^{M} G5(i, j)$$

$$B5_{ave} = \frac{1}{M \times N} \sum_{j=1}^{N} \sum_{i=1}^{M} B5(i, j)$$

Then, in step S903, the detection unit 19 calculates a ratio of $R5_{ave}$ to $G5_a$, namely, $R5_{ave}/G5_{ave}$. In step S904, the color tone selection unit 14 determines whether the ratio $R5_{ave}/G5_{ave}$ output from the detection unit 19 is equal to or higher than a predetermined value, and selects either the first color tone conversion processing or the second color tone conversion processing according to a result of the determination.

The ratio $R5_{ave}/G5_{ave}$ is an example of information indicating an amount of melanin pigment. The ratio also represents a ratio between an information amount of a pigment epithelial layer and an information amount of a choroid. Accordingly, when the ratio $R5_{ave}/G5_{ave}$ is equal to or higher than the predetermined value (YES in step S904), in step S905, the color tone selection unit 14 can determine that a subject's eye belongs to the second group to select the second color tone conversion processing. On the other hand, when the ratio $R5_{ave}/G5_{ave}$ is smaller than the predetermined value (NO in step S904), in step S906, the color tone selection unit 14 can determine that a subject's eye belongs to the first group to select the first color tone conversion processing. The information indicating the amount of melanin pigment may also be acquired by calculating a ratio of intensity of a red distribution returned from the fundus to intensity of a red distribution of the light source. In this case, the color tone selection unit 14 is configured to include a conversion table for associating the ratio of the intensity of the red distribution returned from the fundus to the intensity of the red distribution of the light source with the amount of melanin pigment.

The color tone conversion unit 13 executes either the first color tone conversion processing (step S906) or the second color tone conversion processing (step S905) according to a selection result of the color tone selection unit 14. As described above, the information corresponding to the amount of melanin pigment is detected from the captured original image, and the color tone conversion processing is automatically switched according to the detection result. This provides high usability.

The exemplary embodiment has been directed to the case where at the detection unit 19 and the color tone selection unit 14, the ratio $R5_{ave}/G5_{ave}$ is calculated, and the color tone is selected based on the size of the ratio. However, a ratio $R5_{ave}/B5_{ave}$ may be calculated, and a color tone may be selected based on a size of the ratio. Further, the ratio $R5_{ave}/G5_{ave}$ and the ratio $R5_{ave}/B5_{ave}$ may both be calculated, and a color tone may be selected based on sizes of the ratios.

Figure 6:
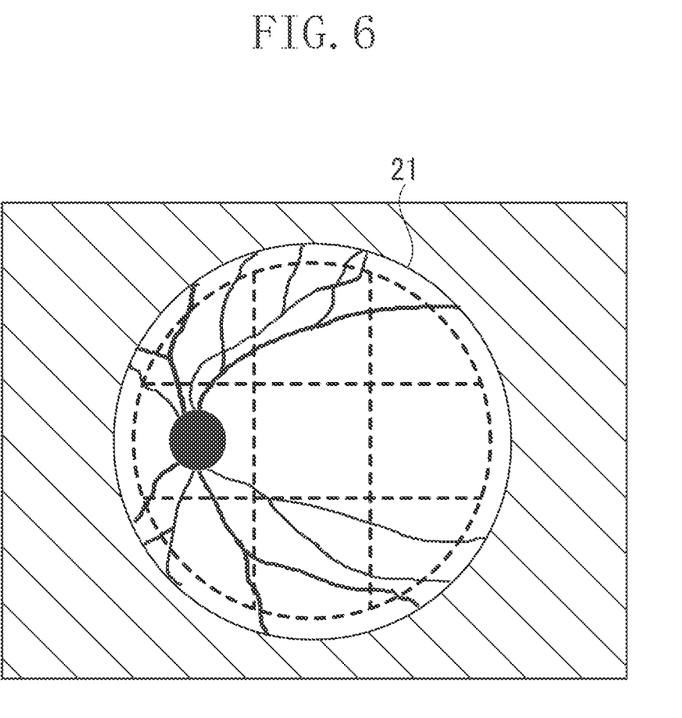
FIG. 6 illustrates division of an image into a plurality of ranges during image acquisition of the range acquisition unit.

The range acquisition unit 20 acquires the image of the predetermined range 23 around the center of the original image. However, as indicated by dotted lines illustrated in FIG. 6, the original image may be divided into a plurality of ranges, and one or a plurality of images can be acquired within the divided ranges. This enables detection of information corresponding to the amount of melanin pigment from an image of a portion other than a lesioned part, namely, a healthy part.

The range acquisition unit 20 may acquire a range where neither any blood vessel nor any papillary portion is represented by using a technology such as pattern matching.

The range acquisition unit 20 acquires the image of the predetermined range around the center of the original image. However, the predetermined range is not necessarily around the center of the original image as a reference.

Figure 7:
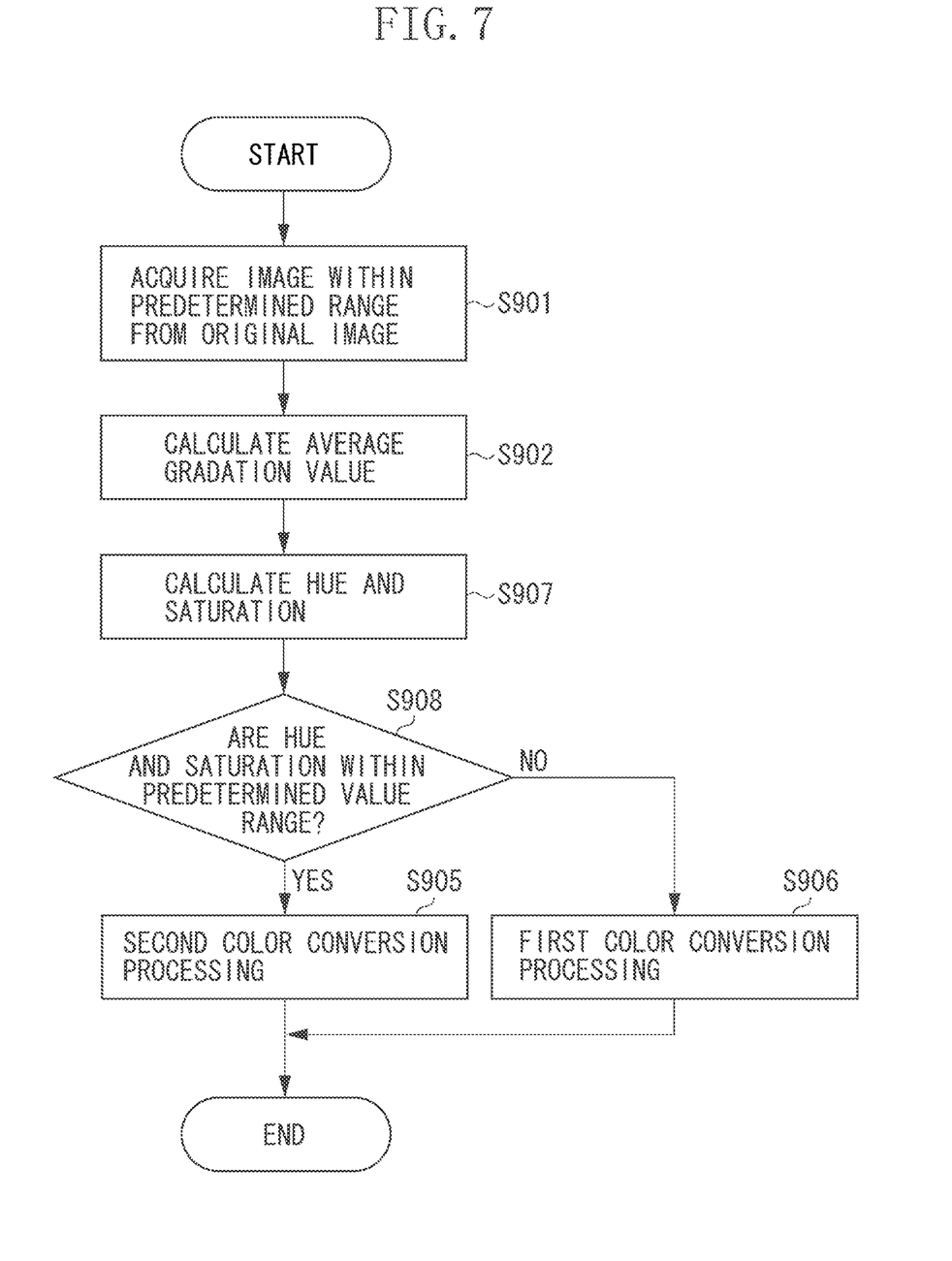
FIG. 7 is a flowchart illustrating an operation of an image processing apparatus according to a third exemplary embodiment.

A third exemplary embodiment will be described. A configuration of the third exemplary embodiment is similar to that illustrated in FIG. 3, and thus description thereof is omitted. The operation will be described referring to a flowchart of FIG. 7. Operations of steps S901, S902, S905, and S906 illustrated in FIG. 7 are similar to those of the second exemplary embodiment, and thus description thereof is omitted.

A detection unit 19 converts average gradation values $R5_{ave}$, $G5_{ave}$, and $B5_{ave}$ for each of red, green and blue channels into a color space where luminance information and color information can be separated from each other. Any color space can be employed as long as color information can be separated from the luminance information. In this exemplary embodiment, an L*a*b color system is used as an example of the color space. The L*a*b color space includes luminance information L and color information *a*b.

Figure 8:
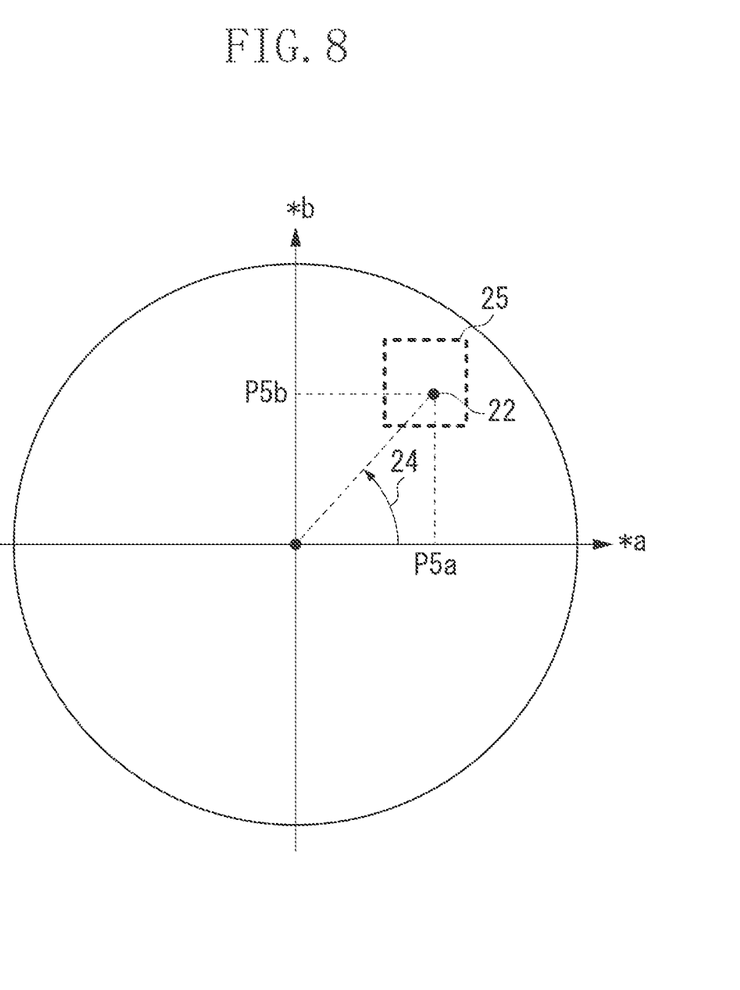
FIG. 8 illustrates plotting of an image acquired by the range acquisition unit on chromaticity coordinates.

When the average gradation values $R5_{ave}$, $G5_{ave}$, and $B5_{ave}$ for each of red, green and blue channels are converted into the L*a*b color space, and its color information is represented by chromaticity coordinates having a horizontal axis *a and a vertical axis *b, the color information is given by coordinates 22 (P5a,P5b) illustrated in FIG. 8. In step S907, saturation and a hue are calculated. On the coordinates 22, the saturation is calculated to be a length of (P5a,P5b), namely, $$\sqrt{P5_a^2 P5_b^2}$$

and the hue is calculated to be an angle 24 between (P5a,P5b) and horizontal axis. In other words, information indicating the amount of melanin pigment can also be acquired from a relationship between the saturation and the hue indicating a distribution in the color space.

In step S908, the color selection unit 14 determines whether the saturation and the hue output from the detection unit 19 are within a range 25 illustrated in FIG. 18. This range 25 indicates a range of tint of a subject's eye belonging to a second group where the amount of melanin pigment is large.

When the saturation and the hue output from the detection unit 19 are within the range 25 (YES in step S908), the second color tone conversion processing corresponding to the second group is selected. On the other hand, when the saturation and the hue output from the detection unit 19 are outside the range 25 (NO in step S908), the first color tone conversion processing corresponding to the first group is selected.

A color tone conversion unit 13 executes either the first color tone conversion processing (step S906) or the second color tone conversion processing (step S905) according to a selection result of the color tone selection unit 14.

As described above, the information corresponding to the amount of melanin pigment is detected from the captured original image, and the color tone conversion processing is automatically switched according to the detection result. This provides high usability.

Figure 9:
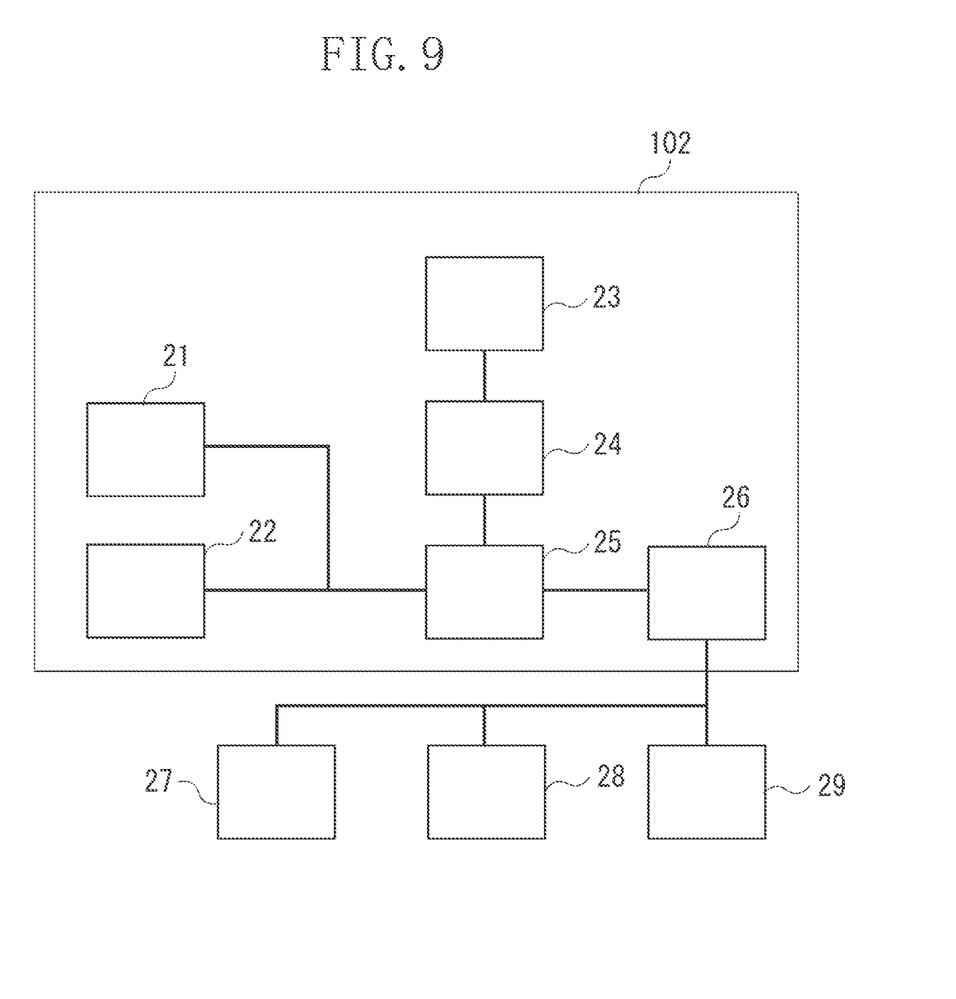
FIG. 9 illustrates a configuration of an ophthalmic imaging system according to a fourth exemplary embodiment.

FIG. 9 illustrates a configuration of a fourth exemplary embodiment. An image adjustment apparatus 102 includes an image acquisition unit 21, an information acquisition unit 22, an image adjustment value setting unit 23, an image adjustment value acquisition unit 24, an image adjustment processing unit 25, and an output unit 26. The output unit 26 is connected to a storage apparatus 27, a display apparatus 28, and a printing apparatus 29.

First, the image adjustment value setting unit 23 will be described.

Figure 10:
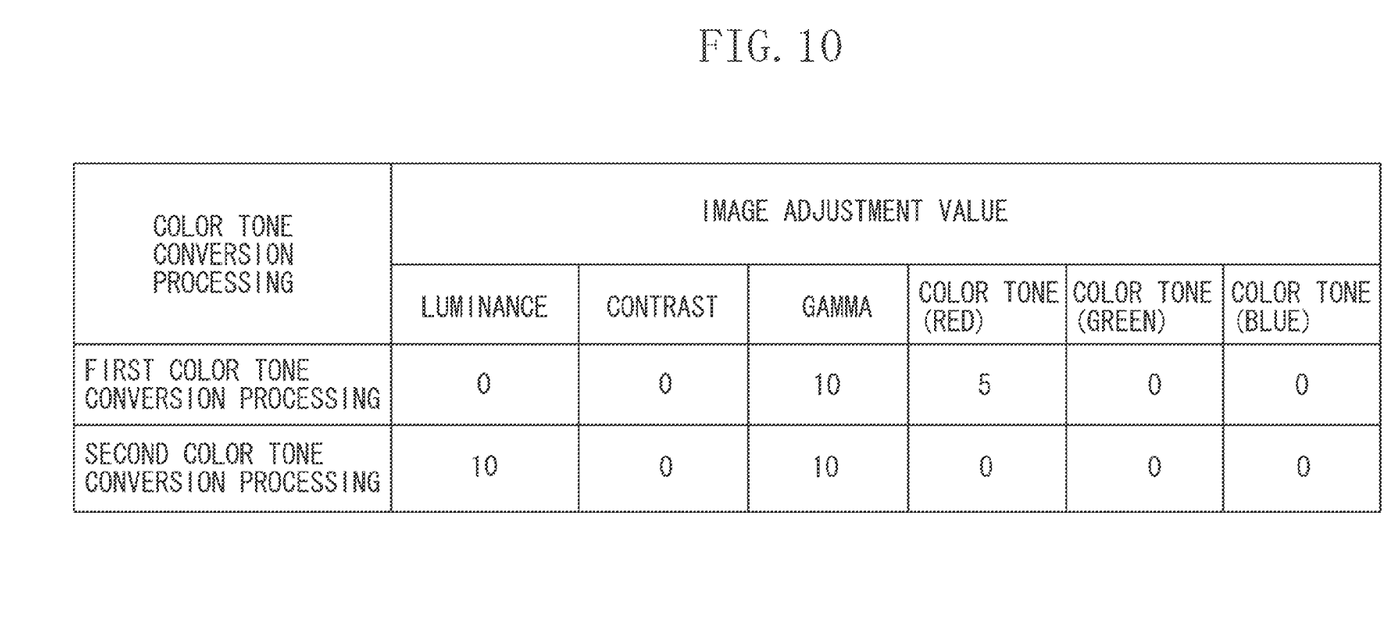
FIG. 10 illustrates an image adjustment value set for each color tone conversion processing.

The image adjustment value setting unit 23 sets an image adjustment value for each color tone conversion processing as illustrated in FIG. 10. Image adjustment values include luminance, contrast, gamma, a color tone (red), a color tone (green), and a color tone (blue). The image setting value is set to align the image in brightness or color when compared with a past image during follow-up observation, and to display and print similar images at a display device and a printing device different from each other in characteristics.

Figure 11:
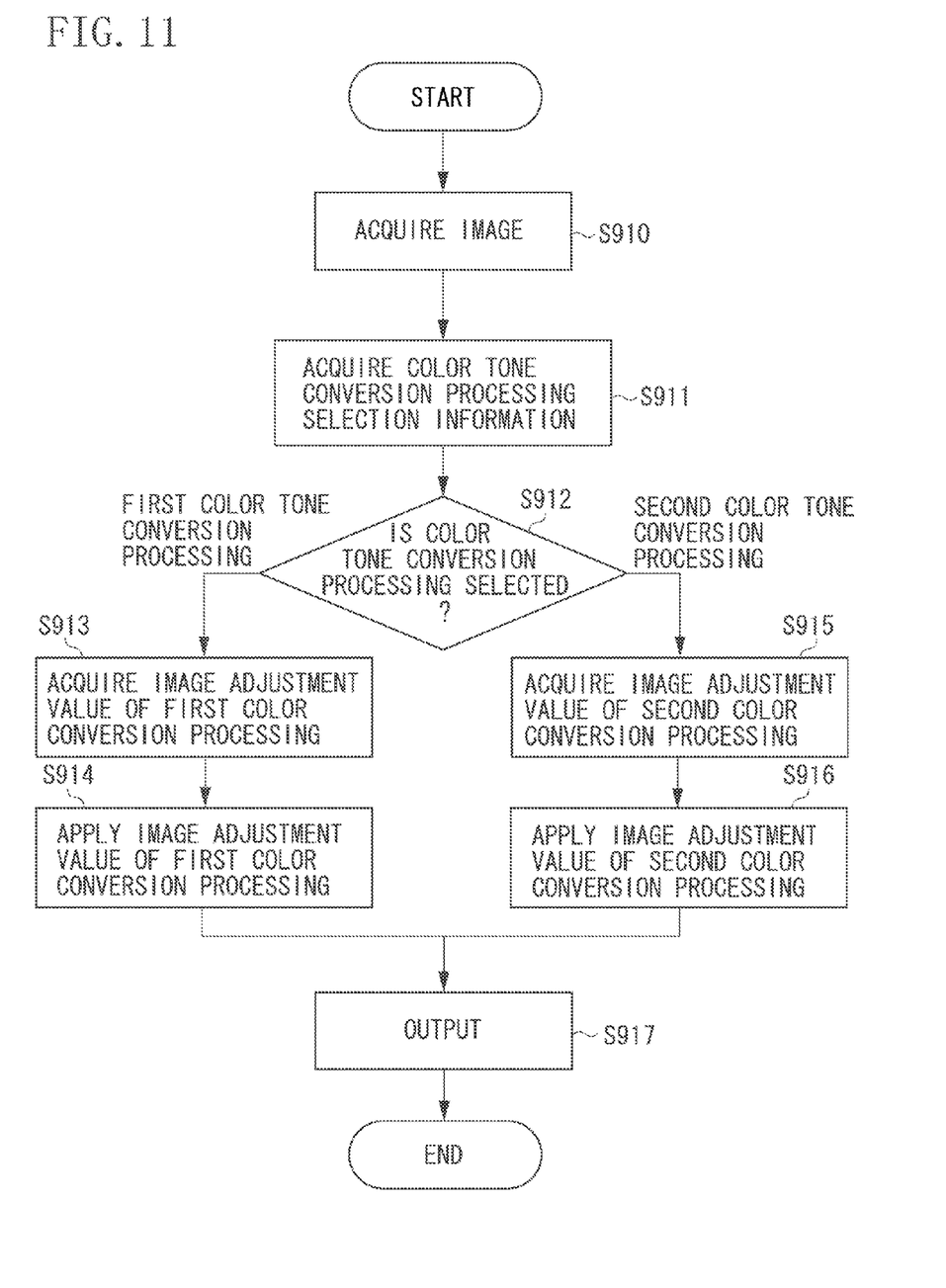
FIG. 11 is a flowchart illustrating an operation of an image processing apparatus according to the fourth exemplary embodiment.

Next, the operation will be described referring to the flowchart of FIG. 11.

In step S910, the image acquisition unit 21 acquires the image stored in the storage unit 18 illustrated in FIGS. 1 and 3.

In step S911, the information acquisition unit 22 acquires color tone conversion processing selection information as to which of first color tone conversion processing and second color tone conversion processing stored in the storage unit 18 illustrated in FIGS. 1 and 3 has been selected.

In step S912, depending on which of the first color tone conversion processing and the second color tone conversion processing the color tone conversion processing selection information acquired by the information acquisition unit 22 is, the image adjustment processing unit 25 selects an image adjustment value to be applied.

In step S913, when the color tone conversion processing selection information is the first color tone conversion processing, the image adjustment value acquisition unit 24 acquires an image adjustment value corresponding to the first color tone conversion processing. In step S914, the image adjustment processing unit 25 applies the acquired image adjustment value corresponding to the first color tone conversion processing to the image acquired by the image acquisition unit 21.

Similarly, in step S915, when the color tone conversion processing selection information is the second color tone conversion processing, the image adjustment value acquisition unit 24 acquires an image adjustment value corresponding to the second color tone conversion processing. In step S916, the image adjustment processing unit 25 applies the acquired image adjustment value corresponding to the second color tone conversion processing to the image acquired by the image acquisition unit 21.

In step S917, the output unit 26 stores the image subjected to the image adjustment processing at the image adjustment processing unit 25 in the storage apparatus 27, displays the image on the display apparatus 28, or outputs the image to the printing apparatus 29.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures, and functions.

This application claims priority from Japanese Patent Application No. 2011-167057 filed Jul. 29, 2011, and Japanese Patent Application No. 2012-144324 filed Jun. 27, 2012, each of which is hereby incorporated by reference herein in its entirety.

What is claimed is:

1. An image processing apparatus for performing image processing on a fundus image of a subject's eye, the image processing apparatus comprising:
   a selection unit configured to select first color tone conversion processing having a first fixed correction value or second color tone conversion processing having a second fixed correction value, wherein a ratio of a red component to a blue component of the second fixed correction value is lower than a ratio of a red component to a blue component of the first fixed correction value, and a ratio of a red component to a green component of the second fixed correction value is lower than a ratio of a red component to a green component of the first fixed correction value; and
   a color tone conversion unit configured to convert a color tone of the fundus image by the first color tone conversion processing with the first fixed correction value or the second color tone conversion processing with the second fixed correction value selected by the selection unit,
   wherein the first color tone conversion processing is for a first eye belonging to a first group and the second color tone conversion processing is for a second eye belonging to a second group, and
   wherein a melanin pigment amount of the second group is smaller than a melanin pigment amount of the first eye.

2. The image processing apparatus according to claim 1, further comprising an acquisition unit configured to acquire information for selecting color tone input by an inspector,
   wherein the selection unit selects either the first color tone conversion processing or the second color tone conversion processing based on the acquired information.

3. The image processing apparatus according to claim 1, wherein the first color tone conversion processing is for a first fundus image of a first eye and the second color tone conversion processing is for a second fundus image of a second eye, and a melanin pigment amount of the second eye is smaller than a melanin pigment amount of the first eye.

4. The image processing apparatus according to claim 1, wherein the selection unit is configured to acquire information indicating a melanin pigment amount according to a distribution of the fundus image in a color space.

5. The image processing apparatus according to claim 1, wherein the selection unit is configured, when either a ratio of a red component to a green component of the fundus image or a ratio of the red component to a blue component of the fundus image is equal to or higher than a predetermined value, to select the second color tone conversion processing.

6. The image processing apparatus according to claim 1, wherein a luminance value represented by red, blue and green color components of the fundus image converted by the first color tone conversion processing is equal to a luminance value represented by red, blue and green color components of the fundus image converted by the second color tone conversion processing.

7. The image processing apparatus according to claim 1, wherein the selection unit is configured, when saturation and a hue in a color space of the fundus image are equal to or higher than predetermined value, to select the second color tone conversion processing.

8. The image processing apparatus according to claim 1, wherein the fundus image is an image acquired by imaging at least a pigment epithelial layer, a nerve fiber layer, and a choroid.

9. The image processing apparatus according to claim 1, wherein the selection unit is configured to select either the first color tone conversion processing or the second color tone conversion processing based on information regarding portions corresponding to a pigment epithelial layer, a nerve fiber layer, and a choroid of the fundus image.

10. The image processing apparatus according to claim 1, further comprising a range acquisition unit configured to acquire a predetermined range in the fundus image,
wherein the selection unit is configured to select either the first color tone conversion processing or the second color tone conversion processing based on an output of the range acquisition unit.

11. The image processing apparatus according to claim 10, wherein the range acquisition unit is configured to divide the fundus image into a plurality of ranges, and to acquire at least one from the plurality of ranges.

12. The image processing apparatus according to claim 1, further comprising a display control unit configured to cause a display unit to display information indicating the first color tone conversion processing or the second color tone conversion processing selected by the selection unit together with the fundus image converted by the color tone conversion unit.

13. The image processing apparatus according to claim 12, further comprising:
an image adjustment value setting unit configured to set image adjustment values associated with the first color tone conversion processing and the second color tone conversion processing; and
an image adjustment processing unit configured to apply the image adjustment value to a fundus image according to information indicating color tone conversion processing stored in association with the fundus image after the color tone conversion processing.

14. An image processing method for performing image processing on a fundus image of a subject's eye, the image processing method comprising:
receiving information by an inspector;
selecting, based on the information, at a selection unit first color tone conversion processing having a first fixed correction value or second color tone conversion processing having a second fixed correction value, wherein a ratio of a red component to a blue component of the second fixed correction value is lower than a ratio of a red component to a blue component of the first fixed correction value, and a ratio of a red component to a green component of the second fixed correction value is lower than a ratio of a red component to a green component of the first fixed correction value; and
converting a color tone of the fundus image by the first color tone conversion processing with the first fixed correction value or the second color tone conversion processing with the second fixed correction value selected by the selection unit,
wherein the first color tone conversion processing is for a first eye belonging to a first group and the second color tone conversion processing is for a second eye belonging to a second group, and
wherein a melanin pigment amount of the second group is smaller than a melanin pigment amount of the first eye.

15. A non-transitory computer-readable storage medium storing a program for causing a computer to perform the image processing method according to claim 14.

* * * * *